US00PP31354P3

(12) United States Plant Patent
Colfer

(10) Patent No.: US PP31,354 P3
(45) Date of Patent: Jan. 14, 2020

(54) ARTICHOKE PLANT NAMED 'PS-MSG0677'

(50) Latin Name: ***Cynara cardunculus* var. *scolymus* L.**
Varietal Denomination: PS-MSG0677

(71) Applicants: PLANT SCIENCES, INC., Watsonville, CA (US); OCEAN MIST FARMS, Castroville, CA (US)

(72) Inventor: William J. Colfer, Aptos, CA (US)

(73) Assignees: PLANT SCIENCES, INC., Watsonville, CA (US); OCEAN MIST FARMS, Castroville, CA (US)

( * ) Notice: Subject to any disclaimer, the term of this patent is extended or adjusted under 35 U.S.C. 154(b) by 0 days.

(21) Appl. No.: 15/932,747

(22) Filed: Apr. 20, 2018

(65) Prior Publication Data

US 2019/0327869 P1 Oct. 24, 2019

(51) Int. Cl.
*A01H 5/02* (2018.01)
*A01H 6/14* (2018.01)

(52) U.S. Cl.
USPC ..... Plt./258
CPC ..... *A01H 6/1432* (2018.05)

(58) Field of Classification Search
USPC ..... Plt./258
CPC ... A01H 5/00; A01H 5/08; A01H 5/04; A01H 5/025; A01H 6/14; A01H 5/02
See application file for complete search history.

(56) References Cited

U.S. PATENT DOCUMENTS

PP24,425 P3 * 5/2014 Colfer ..... A01H 6/14 Plt./258

* cited by examiner

*Primary Examiner* — June Hwu
(74) *Attorney, Agent, or Firm* — Foley & Lardner LLP

(57) ABSTRACT

A new and distinct *Cynara cardunculus* var. *scolymus* L. cultivar of artichoke plant named 'PS-MSG0677', characterized by its fleshiness of bracts; fleshiness of hearts; uniformity of head shapes; and male sterility which is demonstrated by the absence of pollen on all florets during anthesis.

3 Drawing Sheets

Figure 1:
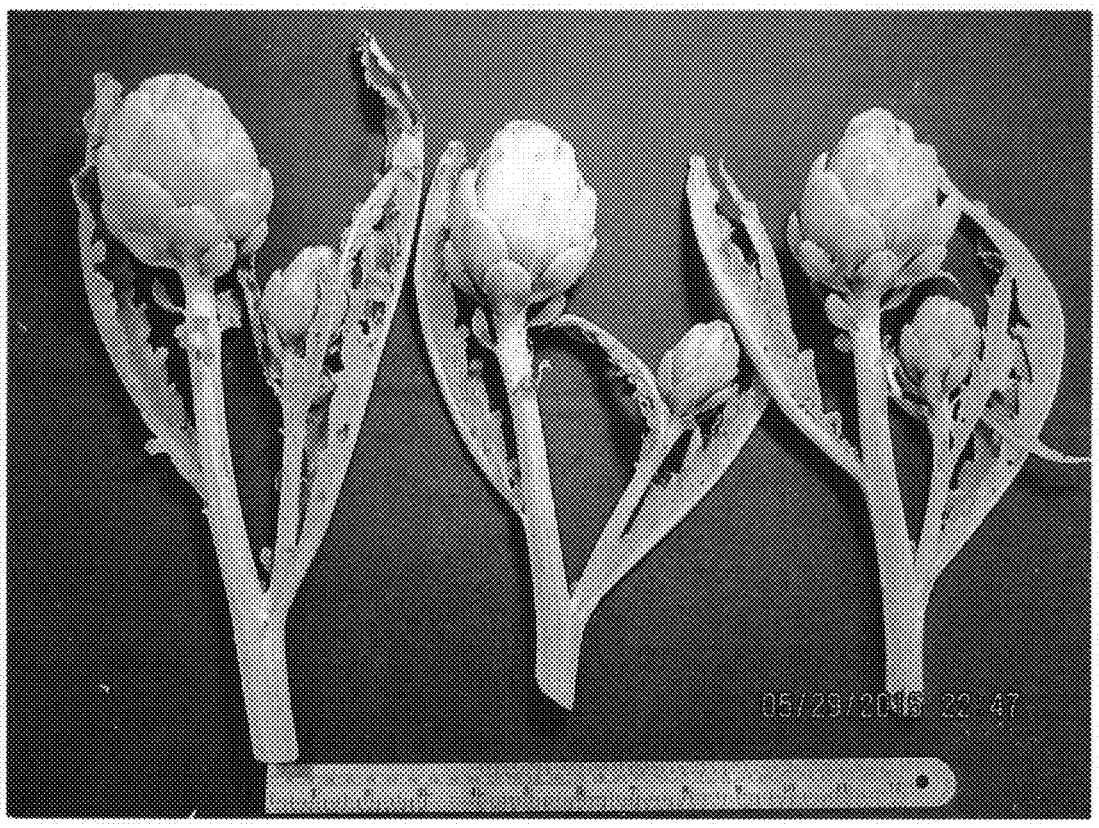

Latin name of the genus and species of the plant claimed: *Cynara cardunculus* var. *scolymus* L.

Variety denomination: 'PS-MSG-0677.'

BACKGROUND OF THE INVENTION

The present invention comprises a new and distinct cultivar of artichoke plant, botanically known as *Cynara cardunculus* var. *scolymus* L., and herein referred to by the cultivar name 'PS-MSG0677.'

*Cynara cardunculus* var. *scolymus* L., commonly known as Globe artichoke, is a thistle-like perennial herb and is a member of the family *Asteraceae*. Globe artichokes comprise: leaves, which are pinnately lobed, but primarily spiny; oval capitula composed of an involucre of overlapping layers of large bracts; and a receptacle, which is enlarged and fleshy. Globe artichoke plants may be propagated by division or vegetative means, and are essentially grown for the production of the immature flower heads, which are considered vegetable delicacies. Fresh artichokes may be baked, steamed, or boiled, after which the fleshy receptacle, inner and outer bracts, and parts of the floral stem may be eaten.

The new artichoke cultivar is a product of a planned breeding program carried out by the inventor, William J. Colfer, in Chowchilla, Calif., in 2007. The new artichoke cultivar 'PS-MSG0677' is a result of a controlled cross between the female (seed) parent, *Cynara cardunculus* var. *scolymus* L. designated 'GGMSC5' (unpatented) and the male (pollen) parent, *Cynara cardunculus* var. *scolymus* L.

designated 'GGRCHB01' (unpatented). The new artichoke 'PS-MSG0677' was discovered and selected by the inventor, as a single flowering plant within the progeny of the stated cross, following several cycles of self-pollination in a controlled environment in 2004/2005 in Merced County, Calif.

Asexual reproduction of the artichoke 'PS-MSG0677' by vegetative cuttings was first performed (in August 2006) in Castroville, Calif., and has demonstrated that the combination of characteristics as herein disclosed for the new cultivar are firmly fixed and retained through successive generations of asexual reproduction. The term "vegetative cutting" refers to the removal of offshoots or suckers from axillary buds borne at the base of the stem just below the soil surface. The new shoots will develop axillary buds and subsequently produce offshoots in the following season. The "vegetative cutting" was removed from the crown region of the new artichoke 'PS-MSG0677.' The new cultivar reproduces true to type.

BRIEF SUMMARY OF THE INVENTION

The following traits have been repeatedly observed and are determined to be unique characteristics of 'PS-MSG0677', which in combination distinguish this artichoke as a new and distinct cultivar:

1. fleshiness of bracts;
2. fleshiness of hearts;
3. uniformity of head shapes; and
4. male sterility which is demonstrated by the absence of pollen on all florets during anthesis.

It should be noted that these data were collected from second-year transplants.

Plants of the new *Cynara* 'PS-MSG0677' differ from plants of the parents, 'GGMSC5' (unpatented) and 'GGRCHB01' (unpatented) in the following characteristics described in Table 1.

TABLE 1

| Characteristic | New Cultivar 'PS-MSG0677' | Female Parent 'GGMSC5' (unpatented) | Male Parent 'GGRCHB01' (unpatented) |
|---|---|---|---|
| Head number | 6.20 | 5.80 | 7.25 |
| Head shape | oval | oval | slightly rounded oval |
| Head color | 5 GY 7/6-5 GY 7/8 | 5 GY 5/4-5 GY 4/4 | 5 GY 4/6-5 GY 6/6 |

Of the many commercial cultivars known to the inventor, the most similar in comparison to the new *Cynara* 'PS-MSG0677' is *Cynara* 'GREEN GLOBE' (unpatented), in the following characteristics described in Table 2.

TABLE 2

| Characteristic | New Cultivar 'PS-MSG0677' | Comparison Cultivar Name GREEN GLOBE (unpatented) |
|---|---|---|
| Average head number | 6.20 | 6.40 |
| Head exterior color | Green yellow (very slight glossiness) | Green (no glossiness) |
| Fleshiness of bract (cm) | 0.54 | 0.51 |

For identification, a series of AFLP molecular markers have been determined for this new artichoke cultivar.

BRIEF DESCRIPTION OF THE PHOTOGRAPHS

The accompanying photographs illustrate the overall appearance of the new artichoke 'PS-MSG0677' showing the colors as true as is reasonably possible with colored reproductions of this type. Colors in the photographs may differ slightly from the color values cited in the detailed botanical description, which accurately describe the color of 'PS-MSG0677'. The depicted plant and plant parts of the new artichoke 'PS-MSG0677' were taken in Merced County, Calif. of second-year transplants.

Figure 2:
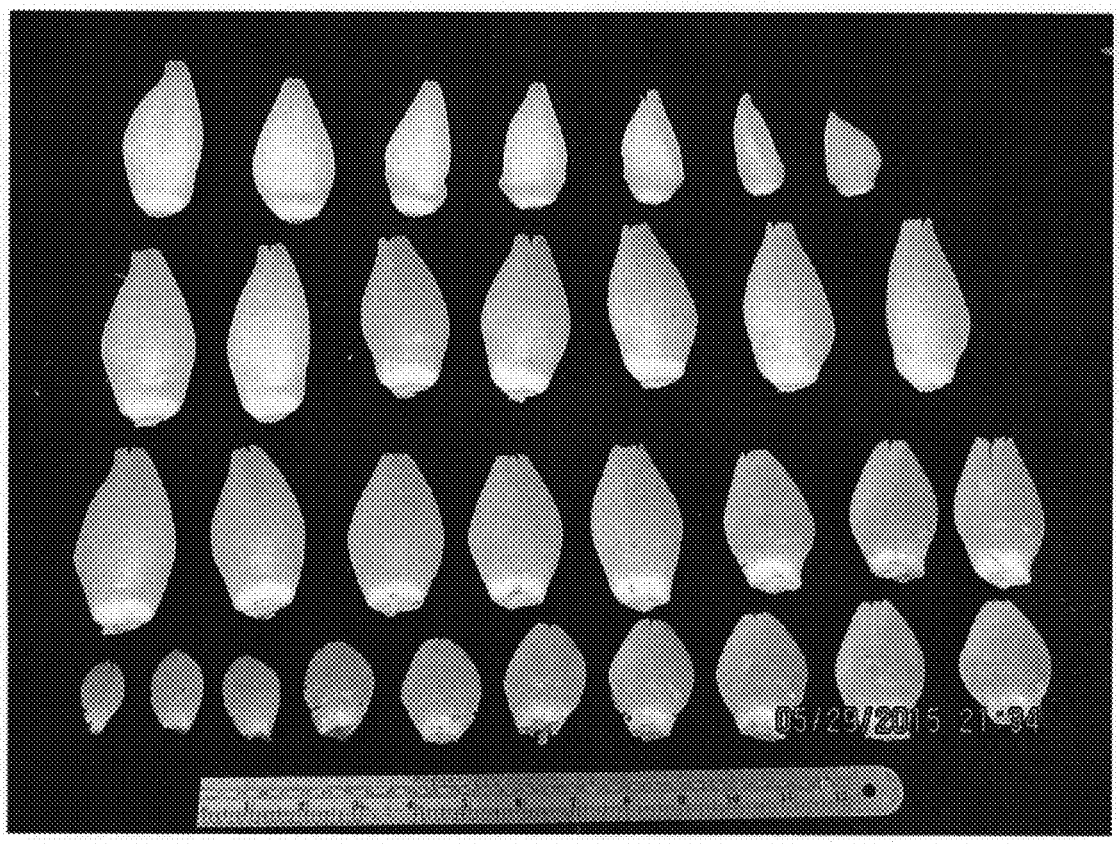
Figure 3:
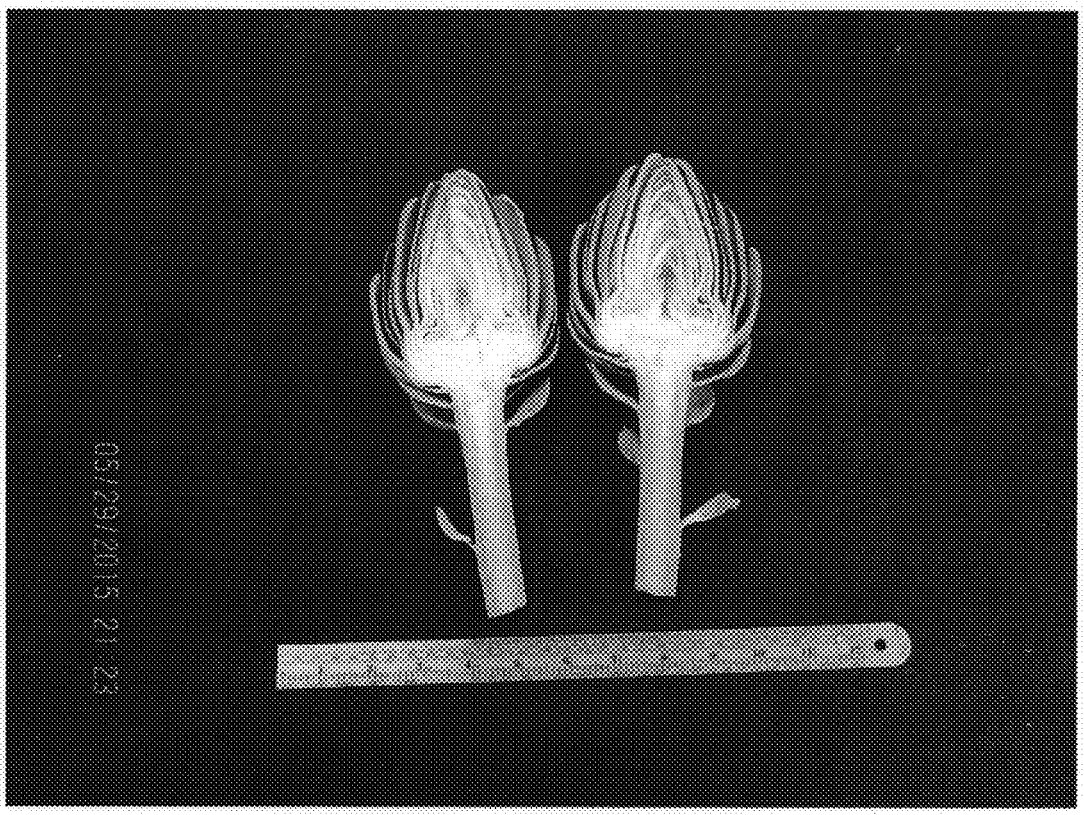

FIG. 1 shows a side view perspective of three 'PS-MSG0677' primary heads with their secondary heads also developing below the larger primary heads;

FIG. 2 shows the bottom row (the most outer bracts) followed by the next layers of bracts (second row) moving inward towards the receptacle. The subsequent rows show the most inner bracts in the third and fourth rows at the top of the page. The artichoke head is an involucre of overlapping layers of bracts, and these bract layers are tightly appressed to each other; and FIG. 3 shows a close-up perspective of typical fruit, with its attached outer bracts (interior appearance).

DETAILED BOTANICAL DESCRIPTION

The new artichoke 'PS-MSG0677' has not been observed under all possible environmental conditions. The phenotype of the new cultivar may vary with variations in environmental factors, including weather (temperature, humidity, and light intensity), day length, soil type, and location, without any change in the genotype of the plant.

The aforementioned photographs, together with the following observations, measurements and values describe plants of 'PS-MSG0677' as grown in Castroville, Calif., under conditions which closely approximate those generally used in horticultural practice.

Castroville is located in California's central coast. Conditions can vary greatly during the summer months. Air temperature can range between the low 20's (degrees Fahrenheit) in the winter to above 80 (degrees Fahrenheit) during the summer months. Relative humidity is generally moderate with values ranging from the mid 40's to the high 60's. Prevailing winds are westerly, and annual rainfall rarely exceeds 25" (inches).

In the following description, holding quality was measured by the physical appearance of the harvested heads. This includes the heads' appearance following 3, 7 and 10-day storage periods in a cold storage room held at 34 (degrees Fahrenheit). Head exterior (oxidation) was observed at each of the three observation points. Browning and blackening of plant tissue was evaluated as light, moderate and extreme. Juiciness was measured by observing exudate and rated as absent, moderate or excessive. Overall storage response was measured by observations concentrated on visible color variability and/or presence of lesions or other cosmetic anomalies. Leaf ratio (L/W) was determined by dividing representative leaf sample length measurements by representative leaf sample width measurements. Finally, head response to weather was determined by observing the heads at maturity. These field observations focus on presence or absence of bronzing, necrotic and chlorotic lesions or any abiotic response to environmental conditions. These data are reported as the possible causal event(s), and then describe the detailed head and plant responses.

The age of the plants in the aforementioned photographs, together with the following observations, measurements and values describe plants of 'PS-MSG0677' about 210-250 days from transplanting. Plants were developed in transplant trays for about 120 to 150 days, for a total plant age of about 330 to 400 days. Not all greenhouse plantings are performed on the same day. Physical data collection may also be performed on different days.

All color references below are measured against The Munsell Book of Color, Munsell Color Macbeth Division of Kollmorgen Instruments Corporation, (1988/PRO88-A). Colors are approximate as color depends on horticultural practices such as light level and fertilization rate, among others.

Classification:

*Botanical.*—*Cynara cardunculus* var. *scolymus* L.

Parentage:

*Female or seed parent.*—*Cynara cardunculus* var. *scolymus* L. designated 'GGMSC5' (unpatented).

*Male or pollen parent.*—*Cynara cardunculus* var. *scolymus* L. designated 'GGRCHB01' (unpatented).

Propagation: Vegetative cuttings (side-shoots selected and harvested from original parent selection).

Plant:

*Height.*—About 92.46 cm. Range: 86.36 cm to 102.24 cm.

*Width.*—About 133.74 cm. Range: 128.88 cm to 147.96 cm.

*Growth habit.*—Upright/intermediate.

*Vigor.*—Good (This measurement is based on overall plant performance, including plant height, density of leaf canopy and overall plant growth and development rates.)

Lateral shoots: These lateral branches from the main stem or offshoots from axillary buds are borne at the base of the stem just below the soil surface.

*Number per plant.*—About 2 or 3 per plant.

*Length.*—About 14.40 cm. Range: 12.07 cm to 16.51 cm.

*Diameter.*—About 2.86 cm. Range: 2.50 cm to 3.10 cm.

*Color.*—5 GY 7/4-5 GY 5/4. Anthocyanin coloration range: 5 R 4/4-5 R 5/4.

*Foliage density.*—Open to moderate, variable shoots give plant an open to moderate plant density appearance.

*Side-shoot development.*—Moderate side-shoot development. Plant responds to floral stalk removal inducing side-shoot development.

*Number of leaves per side-shoot.*—Range: 0 to 3.

Stem (main):

*Length.*—About 6.77 cm. Range: 6.50 cm to 7.2 cm.

*Diameter.*—About 2.86 cm. Range: 2.50 cm to 3.20 cm.

*Width* (*with leaves*).—Ranges from 3.72 cm to 4.80 cm.

*Color.*—Color designation: 5 GY 7/4-5 GY 6/4. Coloration with basal anthocyanin coloration: 5 R 4/4-5 R 5/4.

*Texture.*—Stem texture can vary from areas that are tomentulose to tomentose. Maturity and presence of surrounding leaf tissue influence stem pubescence.

*Number of leaves per main stem.*—Range: 10 to 14.

*Distance between leaf lobes on stem.*—Range: 1.5 cm to 2.1 cm.

*Internode length.*—Range: 5.72 cm to 11.43 cm (Internode length is influenced by soil conditions (moisture) in the field.)

Buds:

*Shape.*—Typically ovate. Range: slightly round to oval; surrounded by developing leaf tissue.

*Height.*—Range: 9.91 cm average (primary head) to 4.92cm average (secondary head).

*Diameter.*—Range: 4.20 cm to 11.30 cm.

*Color.*—Color dependent on age and exposure to sun Range: 5 GY 7/6-5 GY 7/8.

*Texture.*—Glabrous, with some light pubescence at the base of the buds.

Inflorescence: Mature, meaning grown to point of harvest and ready for consumption.

Florets:

*Number per primary head.*—Range: about 1065 to 1350.

*Overall shape.*—Tubulose, fused basal region anther tubes that flare slightly to a flattened, expanded obtuse apex stigmatic region.

*Width.*—About 1.5 mm.

*Color.*—Purple-blue, color dependent on floret age. Range: 10 PB 4/12-10 PB 4/8-10 PB 5/6. Florets oxidize to darker stigmatic colors and lighter anther colors late in maturation.

*Margin.*—Smooth.

*Texture.*—Smooth.

Capitulum (head):

*Number.*—About 6.20/plant. Range: 5.0 to 7.0 heads/plant.

*Shape.*—Predominately oval shapes, and slightly broadened mid-sections, creating rounded oval to oval shape.

*Size.*—(18) Primary: 28.58 cm to 30.40 cm. (24) Secondary: 31.12 cm to 33.02 cm. (30) Tertiary: 28.58 cm to 30.48 cm. (36) Tertiary: 26.04 cm to 27.94 cm. (48) Tertiary: 23.50 cm to 25.40 cm.

*Texture.*—Intermediate, smooth and slightly glossy.

*Color.*—Range: 5 GY 7/6-5 GY 7/8. Some marginal anthocyanin coloration is visible on the basal portions of bracts. (5 R 3/4-5 R 3/2).

*Fragrance.*—Mild, lightly aromatic. Slightly sweet aroma, freshly-cut, green grass aroma.

*Firmness.*—Heads are firm. Some head types in the spring have reduced firmness.

*Gloss.*—Slight gloss green; tips can yellow surrounding the spine region. Heads overall have a slight gloss green coloration.

*Juiciness.*—Some interior bracts have exudate visible. Most outer bracts and peduncle tissues are absent of exudate.

Peduncle:

*Length.*—Range: 9.5 cm to 13.0 cm.

*Diameter.*—Range: 1.90 cm to 2.20 cm (Primary). Range: 1.30 cm to 1.60 cm (Secondary).

*Color.*—Range: 5 GY 6/4-5 GY 5/4. Deep grooves travel lengthwise modifying color uniformity.

*Texture.*—Early development can be tomentose while later development can be delicately tomentose. Distinct smooth grooves are also evident, running the length of the peduncle.

Bract:

*Number.*—About 73.60 bracts. Range: 68 to 80 bracts.

*Outer bract quantity per capitulum.*—Range: 25-27.

*Inner bract quantity per capitulum.*—Range: 45-47.

*Arrangement.*—Bracts layer and overlap attaching to a fleshy receptacle.

*Length.*—About 7.79 cm (outer); Range: 7.00 cm to 9.2 cm. About 9.47 cm (inner.) Range: 9.0 cm to 10.0 cm.

*Width.*—About 5.27 cm (outer). Range: 5.0 cm to 5.50 cm. About 5.29 cm (inner). Range: 5.0 cm to 5.7 cm.

*Shape.*—Bracts are predominantly oval shaped with some bracts displaying apical splitting and apical notching. Inner bracts display only mild constriction in the basal regions of both inner and outer bracts.

*Texture* (*mid-region*).—Smooth, slight texture.

*Color* (*inner position in capitulum*).—Bract interior coloration: 2.5 GY 6/6-2.5 GY 9/2-10 Y 9/4 (green coloration). Outer bract interior coloration (apex): 10 Y 9/4-10 Y 8.5/6. Slight anthocyanin coloration present in innermost interior bract margins. 5 R 3/4-5 R 3/2.

*Color* (*outer position in capitulum*).—5 GY 6/6-5 GY 5/6 (green coloration). Mid-region to base: 5 GY 7/6-5 GY 7/8(green coloration with basal yellow coloration).

*Firmness.*—Malleable. Bracts are highly flexible. Outer bracts are more flexible.

*Spinosity.*—Present on bract apexes. Spines are described as moderate with rounded bract apexes. Length range: 1.0 mm-2.0 mm.

*Basal thickness.*—About 8.00 mm. Range: 6.00 cm to 8.00 mm.

*Density* (*central head inner bract*).—Medium.

*Depth of apical notching* (*outer bract*).—Shallow.

*Reflexing of tip* (*outer bract*).—Inward.

*Basal height* (*outer bract*).—Medium.

*Bract quantity per capitulum.*—72 average.

Receptacle:

*Bristle length.*—44.50 mm average.

*Bristle color.*—10Y 9/1-5Y 9/2.

*Bristle surface texture.*—Smooth with visible longitudinal striations under the surface of the receptacle.

Heart:

*Description.*—Concave, moderately full. Heart is slightly concave with moderate outer margins.

*Color.*—7.5 Y 9/2.

Pappus:

*Number.*—The pappus attaches at the apical region of the mature seed. Approximately 72-90 pappus filaments per seed. Seed numbers vary — about 857 to 1350 seeds per head. The seed numbers vary greatly (dependent upon weather conditions, pollination, fertilization and seed-set), which consequently influence pappus numbers.

*Length.*—About 15.5 mm. Range: 13.0 mm to 19.0 mm.

*Color.*—Variable white coloration. 10Y 9/2 (base)-10Y 8.5/2 (apex) (colors difficult to match).

Overall cold storage response: Good cold storage response. Very slight oxidation observed.

Cold storage (hold quality): Good. Some very slight brown lesions are visible on outer bracts. Tips are free of necrosis.

Head exterior (oxidation): Good. Only those areas damaged during harvest showed some oxidation. Very slight bract margin discoloration.

Head response (weather): None. Some exterior head damage was observed. Some mechanical head damage was observed from abrasion with other surrounding heads.

Foliage (leaves):

*Shape.*—Irregular, dentate leaves that are long and strap-like, parted pinnatisect margins, a slightly reduced tomentose upper-leaf surface and more advanced tomentose lower-leaf surface. The leaf apex is described as a reduced mucronulate.

*Length.*—About 32.42 cm. Range: 30.75 cm to 33.50 cm.

*Width.*—About 14.75 cm. Range: 13.50 cm to 16.60 cm.

*Leaf ratio* (*L/W*).—About 2.15 Range: 2.02 to 2.28.

*Leaf area.*—About 478.90 $cm^2$ Range: 436.65 $cm^2$ to 547.80 $cm^2$.

*Leaf serrations.*—About 37.50 mm. Range: 36 mm to 39 mm.

*Leaf distance between serrations.*—About 17.60 mm. Range: 15 mm to 21 mm.

*Leaf basal angle.*—About 55.00° Range: 47.0° to 62.0°.

*Leaf basal thickness.*—About 9.70 mm. Range: 8.00 mm to 11.00 mm.

*Texture.*—Mature leaves are more blistered (verrucose type appearance). Younger, developing leaves are distinctly more verrucose with a more blistered appearance and texture.

*Pubescence.*—Smooth to sparse density. Pubescence on most leaves is indistinct (glabrous appearance). Immature, younger leaves are highly pubescent (more tomentose). Upper leaf: sparse. Lower leaf: dense.

*Color* (*mature*).—Upper surface: Range: 5 GY 4/6-5 GY 4/4 Lower surface: Range: 5 GY 4/6-5 GY 4/4.

*Color* (*immature*).—Upper surface: Range: 5 GY 4/6 Lower surface: Range: 5 GY 4/4.

*Leaf base midrib spines.*—Absent.

*Spine color.*—Range: 5 Y 9/2-5 Y 8.5/2.

Lobes:

*Number per leaf.*—About 16 to 18 (This number can also vary and is influenced by soil types and winter growth conditions.)

*Number of secondary leaf lobes.*—Few.

*Apex shape.*—Apex is acute with a spiny apex depending on leaf maturity and developmental stages in relation to reproductive bolting.

*Base shape.*—Generally described as pinnatisect and lobed.

*Length.*—Range: 16.8 cm to 20.0 cm (dependent upon leaf developmental stages).

*Width.*—Range: 4.0 cm to 7.9 cm.

Venation: Basal regions of the leaf have slightly green coloration. The terminal and apical regions' coloration is green. Both mid-vein and surrounding venation is green colored.

*Pattern.*—White mid-vein (apex) with light green color venation radiating from leaf mid-vein. Venation pattern is described as pinnate.

*Color.*—5 GY 7/6-2.5 GY 9/2 (upper leaf veination); 10 GY 7/6 (lower leaf veination).

Petiole:

*Length.*—About 9.65 cm. Range: 6.7 cm to 12.3 cm.

*Width.*—About 2.30 cm. Range: 2.20 cm to 2.61 cm.

*Diameter.*—About 8.33 mm. Range: about 8.0 mm to 9.0 mm. Color: 2.5 GY 9/2-5 GY 7/4 (upper regions) 5 GY 8/4 (lower regions).

Reproductive organs/seeds: Seed is generally a light tan color with variable black specks on the seed coat. Seeds have an oval (acute basal apex) shape. About 4 to 4.5 mm (w) x 7 to 8 mm (1).

*Pistil length.*—69 mm average.

*Style length.*—15 mm average.

*Style color.* —10 PB 3/8-10 PB 4/8.

*Stigma color.*—10 PB 5/8-10 PB 6/8.

*Stamen length.*—17 mm average.

*Stamen width.*—3 mm average.

*Anther shape.*—Syngenesious (five fused anthers, as an anther tube).

*Anther color.*—10 PB 6/6-10 PB 7/6.

*Ovary length.*—6 mm average.

*Ovary width.*—4 mm average.

*Ovary position.*—Rest vertically into the receptacle.

Weather tolerance: No testing has been conducted. 'PS-MSG0677' may be sensitive to temperatures below 20° F.

Disease/pest resistance: No observations have been made.

Disease/pest susceptibility: No pest or pathogen resistance or susceptibility has been measured.

Market use/shippability: Experimental line used in breeding experimentation — not shipped or open to market use.

General observations: This new artichoke hybrid is a unique type that exhibits the following characteristics. The plants is moderate in height, ranging from 86 cm to 102 cm. The comparative head qualities to California's artichoke variety 'GREEN GLOBE' (unpatented) are green (slightly glossy) (unlike GREEN GLOBE) exterior coloration with basal blush (like GREEN GLOBE), and moderate head numbers. Head numbers range from 5 to 7 heads per plant. Head shape does have slight variation displaying a predominately oval shape and, slightly broadened mid-sections, rounded oval shapes. These slightly glossy heads are produced in the sizes ranging from size (18) primaries, size (24) secondaries and size (30, 36 and 48) tertiaries. Floral stalk development and head numbers can vary. Anthocyanin coloration is not present in innermost interior bract margins. The head spinosity is present on bract apexes within apical notches. Inner bracts also display spines but can be very slightly notched and splitting. The average spine length ranges between 1.0 and 2.0 mm. The plant's upright growth habit is intermediate, but is very vigorous. The canopy's coloration is a deeper green/yellow color. These colors on Munsell Leaf Color Chart range from 5 GY 4/6 to 5 GY 4/4. Leaf spinosity is light to moderate, and categorized as few. Floral stalk development during anthesis produces a purple flower. Flower color varies with flower maturity. The phenotypic characteristics of this cultivar may vary slightly, depending upon variation in the environmental factors, including weather (temperature, humidity and light intensity), day length, soil type, farming practices, location and time of year.

What is claimed is:

1. A new and distinct *Cynara cardunculus* var. *scolymus* L. cultivar of artichoke plant named 'PS-MSG0677', as herein described and illustrated by the characteristics set forth above.

* * * * *